United States Patent
Ouchi et al.

(10) Patent No.: US 7,933,305 B2
(45) Date of Patent: Apr. 26, 2011

(54) DEVICE FOR GENERATING OR DETECTING ELECTROMAGNETIC RADIATION, AND FABRICATION METHOD OF THE SAME

(75) Inventors: Toshihiko Ouchi, Sagamihara (JP); Ryota Sekiguchi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 644 days.

(21) Appl. No.: 11/376,203

(22) Filed: Mar. 16, 2006

(65) Prior Publication Data
US 2006/0214176 A1  Sep. 28, 2006

(30) Foreign Application Priority Data
Mar. 28, 2005 (JP) ................. 2005-090435

(51) Int. Cl.
*H01S 3/08* (2006.01)
(52) U.S. Cl. .......... 372/99; 372/43.01; 372/45.01; 372/50.124; 372/50.21; 257/80; 257/98; 257/E0.068
(58) Field of Classification Search .......... 257/80, 257/98, E33.069, E31.127, E33.067, E33.068; 372/44.01, 43.01, 45.01, 50.124, 50.21, 99
See application file for complete search history.

(56) References Cited

U.S. PATENT DOCUMENTS

| | | | |
|---|---|---|---|
| 5,341,390 A | 8/1994 | Yamada et al. | |
| 5,757,837 A | 5/1998 | Lim et al. | |
| 5,793,485 A * | 8/1998 | Gourley | 356/318 |
| 5,818,066 A | 10/1998 | Duboz | |
| 6,597,017 B1 * | 7/2003 | Seko et al. | 257/79 |
| 6,618,410 B1 | 9/2003 | Fischer et al. | |
| 6,965,626 B2 * | 11/2005 | Tatum et al. | 372/87 |
| 7,152,007 B2 | 12/2006 | Arnone et al. | |
| 2003/0048537 A1 * | 3/2003 | Hulse | 359/590 |
| 2004/0258107 A1 * | 12/2004 | Sherrer et al. | 372/19 |
| 2006/0085159 A1 | 4/2006 | Itsuji et al. | |
| 2006/0085160 A1 | 4/2006 | Ouchi | |
| 2006/0188398 A1 | 8/2006 | Yano et al. | |
| 2006/0197021 A1 | 9/2006 | Ouchi | |
| 2006/0227340 A1 | 10/2006 | Ouchi et al. | |
| 2006/0244629 A1 | 11/2006 | Miyazaki et al. | |

(Continued)

FOREIGN PATENT DOCUMENTS

JP  5-313220  11/1993

(Continued)

OTHER PUBLICATIONS

Official Action dated Oct. 7, 2008 in Japanese Application No. 2005-090435.

(Continued)

*Primary Examiner* — Evan Pert
*Assistant Examiner* — Eduardo A Rodela
(74) *Attorney, Agent, or Firm* — Fitzpatrick, Cella, Harper & Scinto

(57) ABSTRACT

A device for generating or detecting electromagnetic radiation includes a substrate, a gain medium provided on the substrate, a plurality of reflectors for confining electromagnetic radiation at a predetermined frequency range and substantially perpendicular to a face of the substrate, and spacer means for spacing the reflectors from each other at a predetermined distance, with the gain medium being sandwiched between the reflectors. The gain medium has a quantum well structure formed of a semiconductor material, and gives a gain to electromagnetic radiation by transitioning between subbands created in at least a quantum well in the quantum well structure. The spacer means is formed of a material different from a material of the gain medium.

12 Claims, 4 Drawing Sheets

U.S. PATENT DOCUMENTS

| | | |
|---|---|---|
| 2007/0030115 A1 | 2/2007 | Itsuji et al. |
| 2007/0195921 A1 | 8/2007 | Ouchi et al. |
| 2007/0215808 A1 | 9/2007 | Ouchi et al. |
| 2007/0229094 A1 | 10/2007 | Kasai et al. |
| 2007/0235718 A1 | 10/2007 | Itsuji et al. |
| 2007/0252604 A1 | 11/2007 | Ouchi et al. |

FOREIGN PATENT DOCUMENTS

| | | |
|---|---|---|
| JP | 8-116074 A | 5/1996 |
| JP | 9-172227 | 6/1997 |
| JP | 2001-520808 | 10/2001 |
| JP | 2002-514016 | 5/2002 |
| JP | 2002-204027 | 7/2002 |
| JP | 2003-525446 | 8/2003 |
| JP | 2004-140007 | 5/2004 |

OTHER PUBLICATIONS

S. Kumar, et al., "Continuous-wave operation of teraherz quantum-cascade lasers above liquid-nitrogen temperature" Applied Physics Letters, vol. 84, No. 14, pp. 2494-2496 (2004).

U.S. Appl. No. 10/587,261, filed Jul. 26, 2006, Inventors: T. Ouchi, et al.

U.S. Appl. No. 11/632,958, filed Jan. 19, 2007, Inventors: T. Ouchi.

* cited by examiner

DEVICE FOR GENERATING OR DETECTING ELECTROMAGNETIC RADIATION, AND FABRICATION METHOD OF THE SAME

BACKGROUND OF THE INVENTION

1. Field of the Invention

The present invention relates to a device for generating or detecting electromagnetic radiation, such as terahertz (THz) electromagnetic radiation, and a use and fabrication method for such a device. In this specification, the terminology "the terahertz (THz) electromagnetic radiation" or "terahertz (THz) radiation" or "terahertz (THz)" is used for electromagnetic radiation in a frequency range between about 30 GHz and about 30 THz.

2. Description of the Related Background Art

In recent years, non-destructive sensing techniques have been developed using terahertz (THz) radiation. As applications of electromagnetic radiation in the above frequency range, there have been developed imaging techniques for achieving a perspective inspection apparatus capable of being safely used in place of an X-ray imaging apparatus, spectroscopy techniques for acquiring absorption spectrum and complex dielectric constant of a substance to inspect bonding conditions of atoms and molecules thereof, analytic techniques for analyzing biomolecules, and techniques for estimating carrier density and mobility, for example.

There conventionally have been proposed THz generating methods, such as a method of generating THz pulses by irradiating a photoconductive device with ultra-short pulsed laser light, and a method of generating THz continuous radiation at a beat frequency by mixing two laser light at different frequencies. In those methods of converting light into THz radiation, however, output power typically cannot be increased and power consumption typically cannot be decreased, since converting efficiencies are low.

Accordingly, an electromagnetic radiation generating method resembling a method of a semiconductor laser for emitting light has been researched. In this method, current is injected into a solid device having a semiconductor heterostructure, and electromagnetic radiation is directly generated. "Applied Physics Letters, vol. 84, p. 2494, 2004" discloses a long-wavelength laser that employs induced emission due to carrier population inversion between subbands in the conduction band. In this laser, a plurality of quantum well structures having gains are layered to increase gain. The laser is called a quantum cascade laser. Further, this semiconductor device is a laser of an edge emission type, and uses a metallic plasmon waveguide.

Further, Japanese Patent Application Laid-Open No. 8(1996)-116074 (Japanese reference) discloses a small-sized face emission structure in which a cavity using a negative resistance device is formed perpendicularly to a substrate.

However, the device of the above Japanese reference employs a semiconductor substrate with an active layer as the cavity, so that the length of the cavity cannot be flexibly regulated. Further, since its oscillation wavelength is relatively long, loss in the semiconductor substrate is relatively large, and a ratio of its gain region relative to the cavity length is small. Therefore, it is not easy to reduce its oscillation threshold.

SUMMARY OF THE INVENTION

It is an object of the present invention to provide a device for generating or detecting electromagnetic radiation, which is capable of relatively readily reducing an oscillation threshold and which uses intersubband transition, and to provide a use and fabrication method for such a device.

According to one aspect of the present invention for achieving the above object, there is provided a device for generating or detecting electromagnetic radiation, which includes a substrate, a gain medium provided on the substrate, a plurality of reflectors for confining electromagnetic radiation at a predetermined frequency range and substantially perpendicular to a face of the substrate, and spacer means for spacing the reflectors from each other at a predetermined distance, with the gain medium being sandwiched between the reflectors. The gain medium has a quantum well structure formed of a semiconductor material, and gives a gain to electromagnetic radiation by transitioning between subbands created in at least a quantum-well in the quantum well structure. The spacer means is formed of a material different from a material of the gain medium.

The device can be constructed so that when the device is biased below an oscillation threshold, the device can detect the intensity of electromagnetic radiation incident thereon based on a change in the bias voltage or current caused by absorption of the incident electromagnetic radiation thereby. Also, the device can be constructed so that when the device is biased below and nearly close to an oscillation threshold, it can amplify the intensity of electromagnetic radiation incident thereon.

According to another aspect of the present invention for achieving the above object, there is provided a sensing apparatus for sensing characteristics of an object, which includes a generating device for generating electromagnetic radiation, and a detecting device for detecting electromagnetic radiation. The detecting is arranged so as to detect electromagnetic radiation reflected by or transmitted through an object irradiated with electromagnetic radiation generated by the generating device. At least one of the generating device and the detecting device is the above-described device for generating or detecting electromagnetic radiation.

According to still another aspect of the present invention for achieving the above object, there is provided a method of fabricating the above-described device for generating or detecting electromagnetic radiation, which includes a step of growing a semiconductor heterostructure with a gain medium on a first semiconductor substrate in an epitaxial manner, a step of forming a spacer layer on the epitaxial-grown layer to establish a predetermined distance from a surface of the epitaxial-grown layer, a step of forming a first reflective mirror on a surface of the spacer layer, a step of bonding a surface of the first reflective mirror to a second semiconductor substrate, a step of removing the first semiconductor substrate, and a step of forming a second reflective mirror on a surface of the semiconductor exposed by removing the first-semiconductor substrate.

These advantages, as well as others, will be more readily understood in connection with the following detailed description of the preferred embodiments and examples of the invention in connection with the drawings.

DETAILED DESCRIPTION OF THE PREFERRED EMBODIMENTS

Embodiments of the present invention will hereinafter be described with reference to the drawings.

Figure 1:
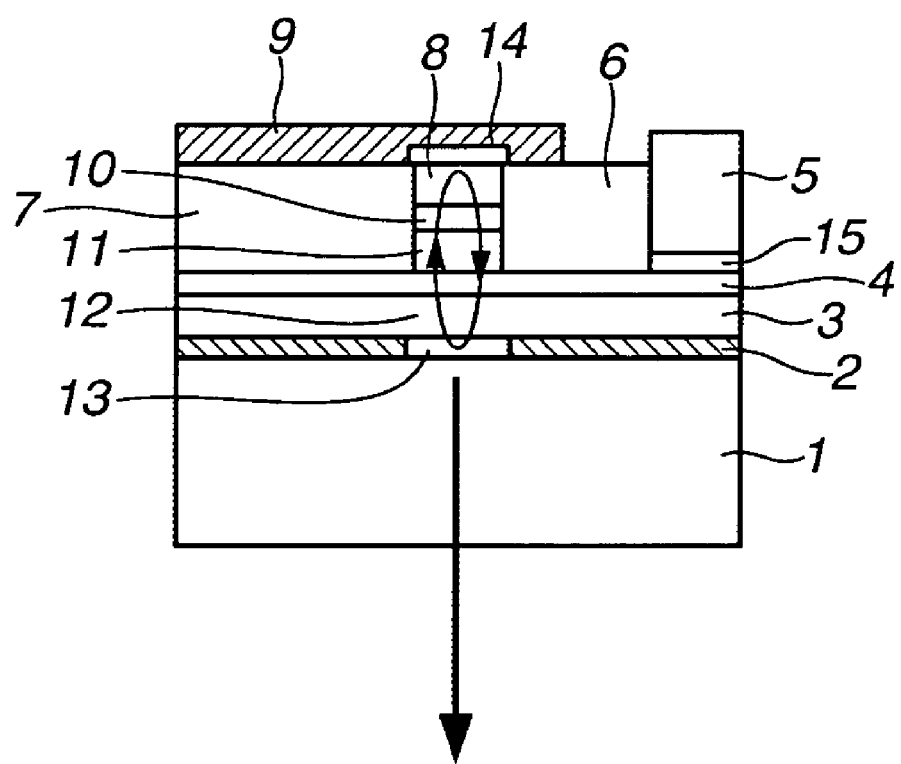
FIG. 1 is a cross-sectional view, taken along a cavity direction, illustrating the structure of a first embodiment of a device for generating or detecting electromagnetic radiation according to the present invention.

FIG. 1 shows a first embodiment of a device for generating or detecting electromagnetic radiation. In the first embodiment, resonance of electromagnetic radiation is created along a resonance direction or cavity direction 12 which is approximately perpendicular to an InP substrate 1, as illustrated in FIG. 1. In the structure of the first embodiment, a spacer layer 3 is provided, and a metallic reflective mirror 2 is arranged between the substrate 1 and an active layer 10.

The active layer 10 has a gain in a terahertz (THz) region due to an intersubband transition of electrons in its conduction band. The active layer 10 has a multi-layer structure that is lattice-matched with the InP substrate 1, and includes an undoped InAlAs of thickness of 4.0 nm, an InGaAs of thickness of 8.4 nm, an InAlAs of thickness of 4.4 nm, an InGaAs of thickness of 5.6 nm, and an InAlAs of thickness of 4.0 nm. Thus, the active layer 10 has a resonant tunneling structure that can generate electromagnetic radiation gain by photon-assisted intersubband transition between quantum wells. Layers 8 and 11 formed on and under the active layer 10 are Si-doped n-type InGaAs contact layers of thickness of 100 nm, respectively.

Further, a layer 4 is an InGaAs layer of thickness of 400 nm that is heavily doped with Si. The spacer layer 3 is composed of an undoped Si of thickness of 33 microns that is formed by sputtering or chemical vapor deposition (CVD). The spacer layer 3 is formed of a crystalline material systems different from materials of the active layer 10 forgiving the gain and other layers. The spacer layer 3 is formed by such a layer depositing method that has a faster deposition rate than the epitaxial growth method or the like, is fit to form a relatively thick layer, and can effectively regulate the cavity length.

A region including the active layer 10 is etched to have a cylindrical shape with a diameter of one (1) micron, and the cylindrical shape is surrounded by portions 6 and 7 formed of a material, such as benzocyclobutene (BCB), that shows a low loss for radiation in a high frequency region, such as THz radiation. Such a cylindrical shape is seen to aid in reducing a floating capacity of the device.

Electrodes 5 and 9 are arranged on the same side of the device. The electrodes 5 and 9 have portions 14 and 15 that are in contact with semiconductor material (i.e., the Si heavily-doped InGaAs layer 4, and the Si-doped n-type InGaAs contact layer 8), respectively. Each of the portions 14 and 15 is formed by depositing Ti to a thickness of 50 nm and then forming a layer of Au thereon. The electrode 5 is composed of a thick layer of Au that has the same height as the electrode 9, as illustrated in FIG. 1. The metallic reflective mirror 2 is an Au thin film with an opening 13 for transmitting electromagnetic radiation formed at its central portion. The reflective mirror 2 is bonded to the Si substrate 1 having a high resistivity.

In the device with the above structure, when a voltage is applied between the electrode 5 and the electrode 9, current is injected into the active layer 10. In the above-discussed structure of the active layer 10, a negative differential resistance appears at a bias voltage near 0.2 V, and the gain can be obtained for THz electromagnetic radiation. Here, the density of the injected current is approximately 5 kA/cm$^2$, and the cavity is established between the Au mirror 2 and the Au mirror 9, that also functions as the electrode. It is accordingly possible to create laser oscillation in a frequency region around 2.5 THz. The cavity length is set at about 34 microns corresponding to a wavelength of electromagnetic radiation. The wavelength shortening effect in the semiconductor is considered to determine this magnitude. The cavity length is appropriately set by the spacer layer 3 having a thickness of 33 microns.

The appearance of the negative differential resistance results from the generation of gain for electromagnetic radiation due to the intersubband transition. The intersubband transition is caused by the tunneling current between wells in the active layer 10 with the triple barrier structure biased at a predetermined voltage.

A fabrication process of the first embodiment will be described with reference to FIGS. 2A to 2H.

Figure 2A:
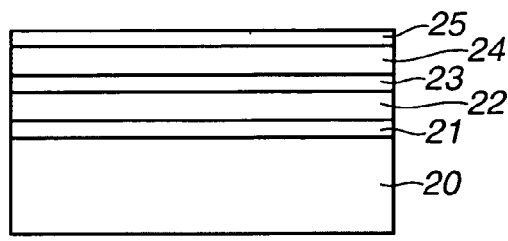
FIGS. 2A to 2H are cross-sectional views schematically illustrating respective steps of a fabrication method of the first embodiment.

As illustrated in FIG. 2A, an InP buffer layer 21, an InGaAs contact layer 22, an active layer 23 with the above-discussed InAlAs/InGaAs multi-layer structure, an InGaAs contact layer 24, and a heavily-doped InGaAs contact layer 25 are grown on an InP substrate 20 in an epitaxial manner using molecular beam epitaxy (MBE) or the like.

Figure 2E:
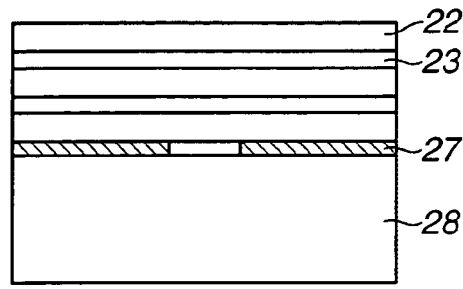
Figure 2B:
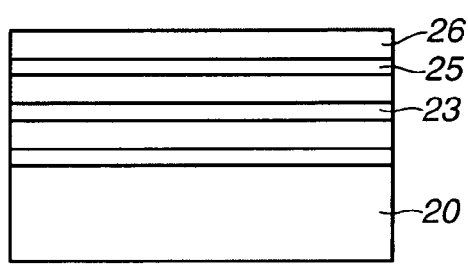

Then, as illustrated in FIG. 2B, an undoped Si spacer layer 26 is formed using chemical vapor deposition (CVD) or the like. An Au thin film 27 for the metallic mirror is then formed, and an opening for transmitting electromagnetic radiation therethrough is formed in the Au thin film 27, as illustrated in FIG. 2C.

Figure 2F:
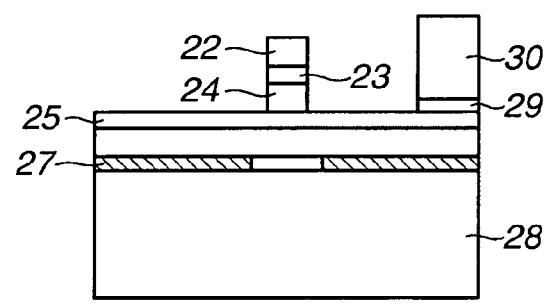
Figure 2C:
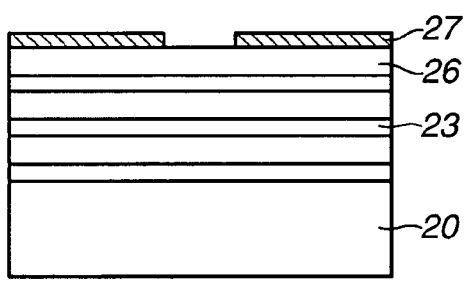
Figure 2G:
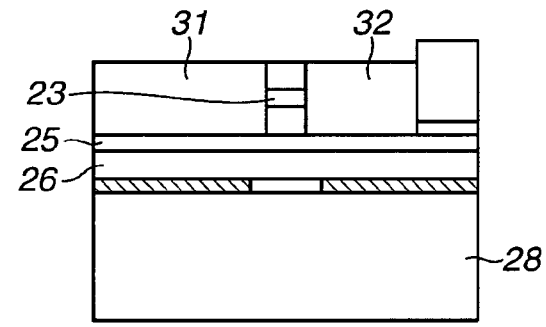
Figure 2D:
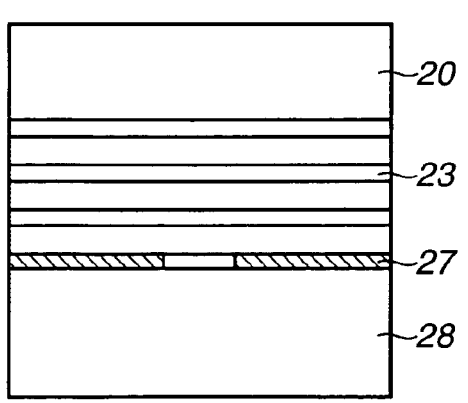
Figure 2H:
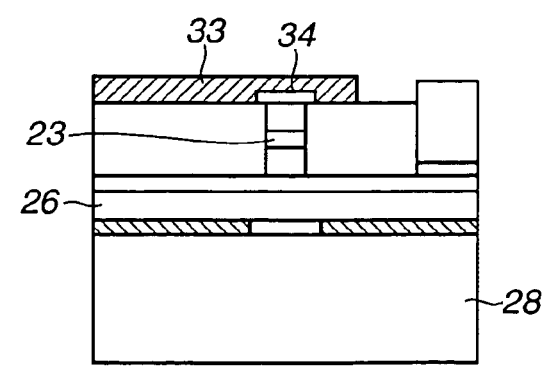

After that, as illustrated in FIG. 2D, the wafer is bonded to a high resistivity Si substrate 28 with the metallic mirror 27 being used as a bonding face. Here, it is possible to employ a bonding method of using a resin adhesive, a method of forming a fittingly-patterned Au thin film on the Si substrate 28 and pressing both the Au thin film 27 and the fittingly-patterned Au thin film against each other, a method of forming a fittingly-patterned Au thin film on the Si substrate 28 and bonding both the Au thin film 27 and the fittingly-patterned Au thin film by, for example, Au—Sn solder, or the like.

Further, as illustrated in FIG. 2E, the InP substrate 20 and the InP buffer layer 21 are removed by wet etching using a solution of hydrochloric acid and water (its ratio is 1:1), or chemical mechanical polishing (CMP) In the case of the wet etching, the etching rate of the InGaAs contact layer 22 for an etchant of hydrochloric acid material systems is low, so that the etching can be selectively stopped at a surface of the InGaAs layer.

Then, a cylindrical pole with a diameter of one micron is formed by performing etching down to the InGaAs high-doped contact layer 25 using photolithography and plasma etching of chlorine systems, as illustrated in FIG. 2F. Further, Ti 29 and Au 30 are formed by lift-off to form a lower electrode on a portion of the exposed contact layer 25.

Thereafter, as illustrated in FIG. 2G, deposition and etching for partial exposure are performed to surround the cylindrical post with BCB 31 and 32. Titanium (Ti) 34 is then formed covering a top of the cylindrical post only, and Au 33 is formed overall by lift-off, as illustrated on FIG. 2H. Finally, annealing of the wafer is carried out at about 400 degrees C. to improve the electrode contact.

In the above fabrication method, the spacer layer 26 is deposited on the surface of epitaxial layers including the active layer 23, using the CVD or the sputtering, and the first reflective mirror 27 is formed on the spacer layer 26. With respect to the second reflective mirror, after the first substrate 20 used for the epitaxial growth is bonded to the second substrate 28, the second reflective mirror is formed after the first substrate 20 is removed, for example.

In such a structure, since the Si layer or the like with reduced loss for electromagnetic radiation is formed by a process different from the epitaxial process for epitaxially growing the active layer, the cavity length can be effectively and efficiently adjusted to any appropriate length. Further, a volume ratio between the gain medium and the passive region without gain can be appropriately regulated. In other words, in a space of the structure for confining the electromagnetic radiation between the metallic reflective mirrors, the active layer can be selectively located at a region with a strong amplitude of the electromagnetic radiation (an optimum position of a loop of the resonance). Hence the oscillation threshold can be effectively reduced.

Although a single active layer is employed in the above construction, it is possible to use a structure in which a plurality of active layers are layered with thin contact layers interposed therebetween for purposes of enhancing the gain. Further, the spacer layer can be formed of a material with small loss for THz radiation, such as dielectric material, other than the high resistivity Si. The dielectric material can be selected from BCB, polypropylene, fluorine-contained polymers, polyethylene, or other organic resin, for example. Also, the spacer layer can be formed of heat resistant ceramics, such as alumina and aluminum nitride. The heat resisting property is preferred for resisting temperatures during the fabrication process of the device.

In the above device for generating electromagnetic radiation with a resonant structure extending approximately perpendicular to the substrate, the spacer layer that can be readily regulated in thickness is interposed between the active layer and the mirror on the substrate side. The spacer layer, however, can be provided between the active layer and the other mirror on a side opposite to the substrate side.

As for the reflective mirrors, it is possible to employ a structure using three or more mirrors, such as a structure in which a mirror is arranged on one side of the active layer and two mirrors forming a predetermined angle therebetween are arranged on the other side of the active layer. Furthermore, it is not necessary for all the reflective mirrors to be metallic mirrors. It is allowable that only at least one reflective mirror is a metallic mirror.

In the above discussions, the structure is acted as an oscillator or a device for generating electromagnetic radiation. It is, however, possible to operate the above structure as a device for detecting THz radiation, or an amplifier for amplifying THz radiation, when excited by a bias below the threshold. When the bias is relatively far from the threshold, the structure can act as the detector. When the bias is set very close to the threshold, the structure can act as the amplifier. With respect to material systems, it is also allowable to use strained AlAs systems as the barrier layer, or use different material systems, such as AlGaAs/GaAs systems and GaN/InN systems.

According to the above embodiment, a radiation generating device and the like can be achieved in which the intersubband transition is used, and losses in the substrate and the spacer layer are reduced, leading to reduced loss in the cavity. Accordingly, in the radiation generating device, the oscillation threshold can be lowered.

Figure 3:
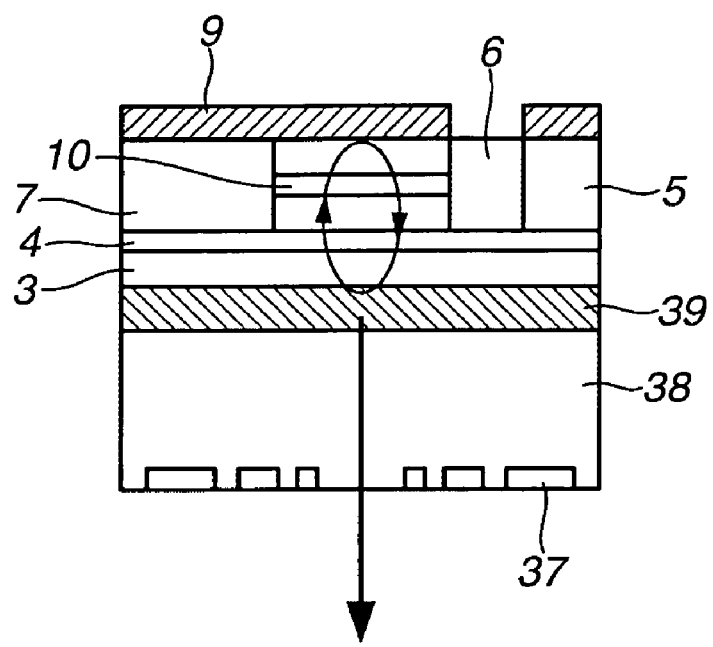
FIG. 3 is a cross-sectional view, taken along a cavity direction, illustrating the structure of a second embodiment of a device for generating or detecting electromagnetic radiation according to the present invention.

FIG. 3 shows a second embodiment of a device for generating or detecting electromagnetic radiation according to the present invention. In FIG. 3, portions having the same functions as those of the first embodiment illustrated in FIG. 1 are designated by the same reference numerals. In the second embodiment, a dielectric multi-layer is used as a reflective mirror 39 having the same function as the reflective mirror 2 in the first embodiment, and provided between a substrate 38 and layers including the active layer 10. This multi-layer is composed of six BCB layers with a low dielectric constant and a thickness of 20 microns, and six Si layers with a high dielectric constant and a thickness of 8.6 microns. The BCB layer and the Si layer are alternately layered. A quarter-wavelength multi-layer mirror for THz radiation at 2.5 THz (wavelength is 120 microns) is thus constructed. It should be noted that the materials, thicknesses, and the number of layers are not limited to those described above.

In the second embodiment, a Fresnel lens 37 for converging an emitted radiation beam is formed on a radiation emerging surface of the substrate 38, using etching or the like. In place of the Fresnel lens 37, an external lens can be used. This also holds true in other embodiments.

When the above dielectric multi-layer mirror is employed, there is no need to form an opening for transmitting electromagnetic radiation therethrough. Further, the reflectivity of the mirror can be regulated over a wide range by selecting materials and the number of layers in the multi-layer mirror. Therefore, the structure can be flexibly determined depending on the type of the device, i.e., a low threshold type or a high output type. For example, the low threshold type can be achieved when the number of layers is increased to enhance the reflectivity. Alternatively, the high output type can be achieved when the reflectivity on the radiation emitting side is reduced. The second embodiment is similar to the first embodiment in the other aspects.

Figure 4:
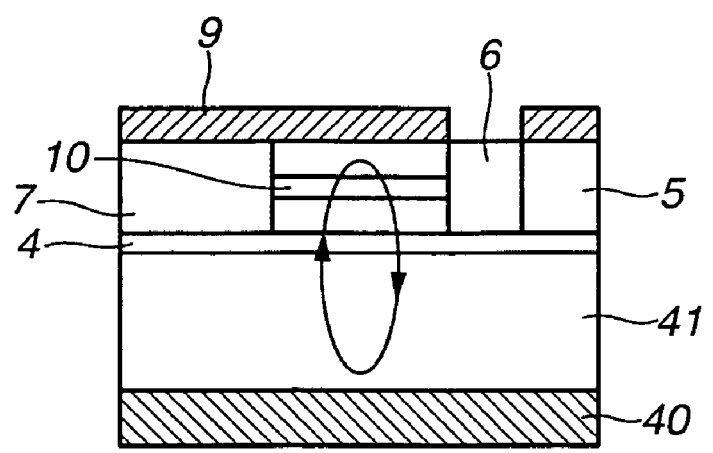
FIG. 4 is a cross-sectional view, taken along a cavity direction, illustrating the structure of a third embodiment of a device for generating or detecting electromagnetic radiation according to the present invention.

FIG. 4 shows a third embodiment of a device for generating or detecting electromagnetic radiation according to the present invention. In FIG. 4, portions having the same functions as those of the first embodiment illustrated in FIG. 1 are designated by the same reference numerals. In the third embodiment, a dielectric mirror 40 is formed on a substrate 41 that is included in the cavity. The substrate 41 is formed by shaping a dielectric body with a small absorption for THz radiation into a desired thickness (i.e., the substrate 41 also functions as the spacer layer). In the third embodiment, a high resistivity Si substrate polished to a thickness of about 100 microns is used as the substrate 41, for example.

As the oscillation wavelength increases, for example, close to about a wavelength corresponding to 1 THz, the thickness of the substrate 41 forming the cavity also increases. Accordingly, the cavity length can be readily adjusted only by polishing the substrate, and hence a fabrication process of the device can be simplified. With respect to the other aspects, the third embodiment is similar to the first embodiment.

Figure 5:
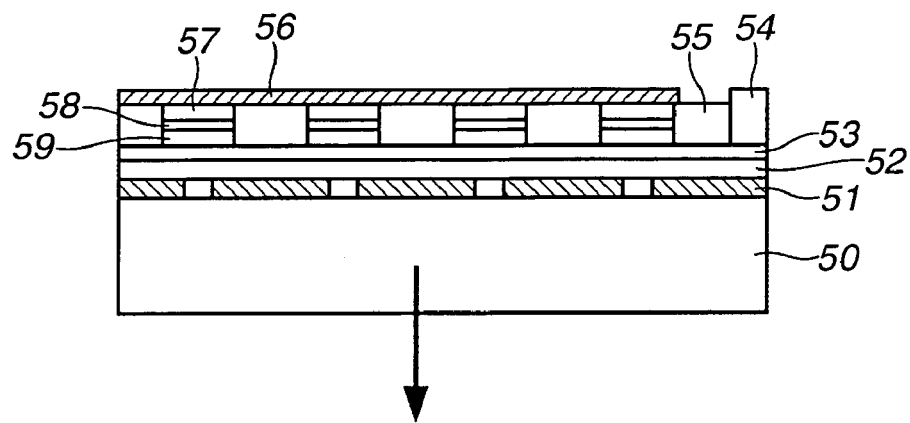
FIG. 5 is a cross-sectional view, taken along a cavity direction, illustrating the structure of a fourth embodiment of a device for generating or detecting electromagnetic radiation according to the present invention.

FIG. 5 shows a fourth embodiment of a device for generating or detecting electromagnetic radiation according to the present invention. In the fourth embodiment, a plurality, of oscillating devices are arranged in a parallel manner to increase a laser output. Common electrodes 54 and 56 cause a current flow into each device that has the same function as the device of the first embodiment.

In other words, the device of the fourth embodiment includes a substrate 50, a metallic mirror layer 51 with a plurality of openings, a spacer layer 52, an Si-high-doped InGaAs layer 53, Si-doped n-type InGaAs contact layers 57 and 59, active layers 58 with a quantum well structure having a semiconductor heterostructure, and burying layers 55. The active layer 58 generates a gain for electromagnetic radiation due to transition between subbands created in quantum wells in the quantum well structure. When the respective devices are provided at intervals of less than about 100 microns that is the oscillation wavelength, electromagnetic radiation is oscillated from the respective devices with a common-phase relationship maintained therebetween. Therefore, respective electromagnetic radiation waves interfere with each other so that a single beam of electromagnetic radiation can be emitted.

In the above structure, it is possible to cause oscillation and emission of electromagnetic radiation having such high output power that it cannot be obtained by a single device. The fourth embodiment is similar to the first embodiment in the other aspects.

Figure 6:
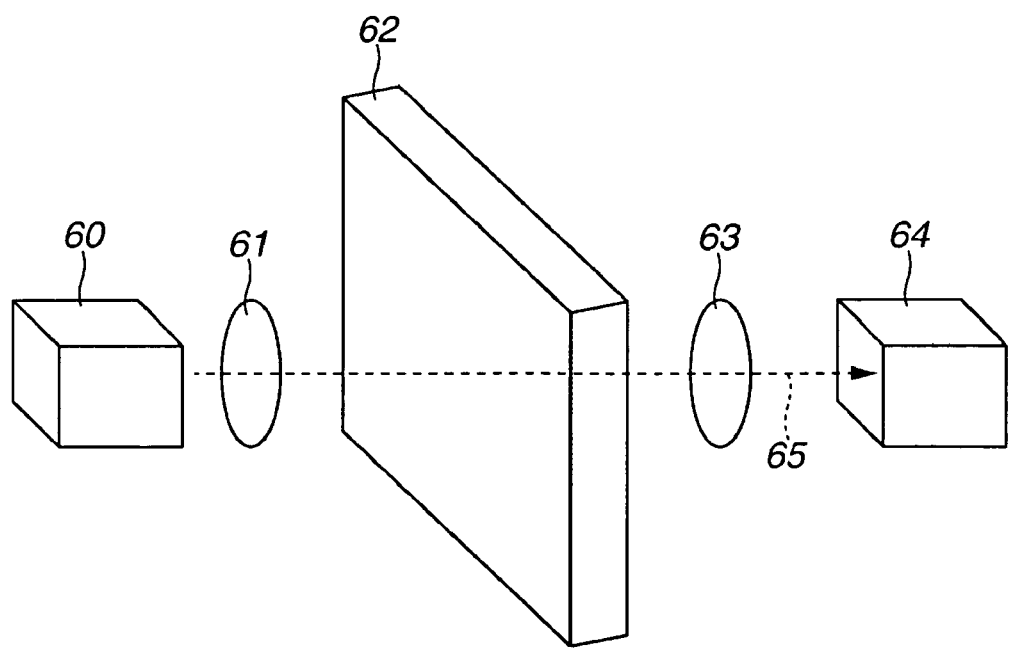
FIG. 6 is a perspective view schematically illustrating the structure of a fifth embodiment of a sensing apparatus according to the present invention.

FIG. 6 shows a fifth embodiment of a sensing system of a desired type in which THz radiation lasers of the above embodiments are used for generation and detection of THz electromagnetic radiation. In the sensing system of the fifth embodiment, a device 60 for generating THz radiation constructed according to the present invention is used, an object 62 to be investigated is placed behind a lens 61 for converging a THz beam from the device 60, and a lens 63 for converging the THz beam and a detector 64 are provided along a radiation propagating direction 65 on a side opposite to the side of the device 60 for generating THz radiation.

The detector 64 has approximately the same structure as the THz generating device 60, and the reflectivity of a mirror on a radiation incident side of the detector 64 is appropriately reduced. The detector 64 is operated under a condition under which its bias voltage is set below its threshold. Here, the detector 64 can be operated as an amplifier for amplifying the intensity of radiation at the same frequency by appropriately setting the bias voltage. It is possible to use an Si bolometer, a Golay cell, a photoconductive device, or the like as the detector 64. Further, when the THz generating device 60 and the detector 64 are arranged side by side, a sensing system can be established in which THz radiation reflected by the object 62 is detected by the detector 64.

In the above sensing system using THz radiation, identification of characteristics of paper, polymer, biomolecule, medicine, or the like can be carried out in a non-contact and non-destructive manner. Further, identification of characteristics of an object hidden in another object, which cannot be confirmed with visible light, can be performed together with imaging thereof, for example.

Conventionally, those measurements were performed by a method using excitation by a large-sized femtosecond laser. When devices for generating or detecting electromagnetic radiation according to the present invention are used, the size can be reduced and power consumption can be decreased.

As described in the foregoing, according to the present invention, spacer means is composed of a material different from the gain medium, so that the cavity length can be regulated relatively efficiently. Accordingly, the oscillation threshold of a device for generating or detecting electromagnetic radiation using the intersubband transition can be relatively readily reduced. Particularly, the device can be readily functioned as a source for highly efficient generation of THz radiation, and such a device can be widely used in various sensing applications. Further, when the device is used below the threshold, the device can be used as a highly-efficient amplifier or detector.

While the present invention has been described with respect to what is presently considered to be the preferred embodiments and examples, it is to be understood that the invention is not so limited. The present invention is intended to cover various modifications and equivalent arrangements included within the spirit and the scope of the appended claims.

This application claims priority from Japanese Patent Application No. 2005-90435, filed Mar. 28, 2005, which is hereby incorporated by reference.

What is claimed is:

1. A device for generating or detecting a terahertz wave, said device comprising:
    a substrate;
    a gain medium provided on the substrate, said gain medium having a quantum well structure formed of a semiconductor material, and said gain medium giving a gain to the terahertz wave by transition between subbands created in at least a quantum well in the quantum well structure;
    a plurality of reflectors for confining the terahertz wave in a predetermined frequency range substantially perpendicularly to a face of the substrate; and
    a spacer layer for spacing the reflectors from each other at a predetermined distance with the gain medium being sandwiched between the reflectors, said spacer layer being formed of a material different from a crystalline material of the gain medium,
    wherein the predetermined distance between the reflectors is determined by a thickness of the spacer layer such that the predetermined distance approximately equals to an equivalent wavelength of the terahertz wave in the device,
    wherein the spacer layer is composed of Si, organic resin, or ceramics,
    wherein the terahertz wave is reflected in a reflection area on at least one reflector among the plurality of reflectors, and
    wherein the reflection area on the at least one reflector is in contact with the spacer layer.

2. The device according to claim 1, wherein said gain medium has a resonant tunneling structure that can generate the gain for the terahertz wave by photon-assisted intersubband transition between quantum wells.

3. The device according to claim 1, further comprising current injecting means for injecting current into the gain medium between the reflectors so that the terahertz wave can be generated.

4. The device according to claim 1, wherein the device is constructed so that when it is biased below an oscillation threshold, it can detect the intensity of the terahertz wave incident thereon based on a change in the bias voltage or current caused by absorption of the incident terahertz wave thereby.

5. The device according to claim 1, wherein the device is constructed so that when it is biased below and nearly close to an oscillation threshold, it can amplify the intensity of the terahertz wave incident thereon.

6. A sensing apparatus for sensing characteristics of an object, said sensing apparatus comprising:
    a generating device for generating the terahertz wave; and
    a detecting device for detecting the terahertz wave, said detecting device being arranged so as to detect the terahertz wave reflected by or transmitted through an object irradiated with the terahertz wave generated by the generating device, wherein at least one of the generating device and the detecting device is the device for generating or detecting the terahertz wave as recited in claim 1.

7. A method of fabricating the device for generating or detecting electromagnetic radiation as recited in claim 1, said method comprising the steps of:

growing a semiconductor heterostructure with a gain medium on a first semiconductor substrate in an epitaxial manner;

forming a spacer layer on the epitaxial-grown layer to establish a predetermined distance from a surface of the epitaxial-grown layer;

forming a first reflective minor on a surface of the spacer layer;

bonding a surface of the first reflective mirror to a second semiconductor substrate;

removing the first semiconductor substrate; and forming a second reflective minor on a surface of the semiconductor exposed by removing the first semiconductor substrate.

8. A device for generating a terahertz wave comprising:

a first reflective minor for reflecting the terahertz wave;

an epitaxial-growth layer grown in an epitaxial manner on the first reflective minor, the epitaxial-growth layer including a gain medium for giving a gain to the terahertz wave by transitioning between subbands created in at least a quantum well in a quantum well structure formed of a semiconductor material;

a spacer layer formed on a surface of the epitaxial-growth layer, the spacer layer being formed of a material different from a crystalline material of the gain medium; and a second reflective minor provided on a surface of the spacer layer in order to confine the terahertz wave between the first reflective minor and the second reflective minor in a direction substantially perpendicular to an in-plane direction of the gain medium, wherein a distance between the first reflective minor and the second reflective mirror is determined by a thickness of the spacer layer such that the distance approximately equals to an equivalent wavelength of the terahertz wave in the device, wherein the spacer layer is composed of Si, organic resin, or ceramics, wherein the terahertz wave is reflected in a reflection area on at least one reflector among the plurality of reflectors, and wherein the reflection area on the at least one reflector is in contact with the spacer layer.

9. A device according to claim 8, further comprising:

a substrate formed of a material with small loss for the terahertz wave taken out from the second reflective mirror; and a lens provided on a surface of the substrate opposite to a surface of the substrate on which the second reflective minor is provided in order to converge the terahertz wave taken out from the second reflective minor.

10. A device according to claim 8, wherein the second reflective mirror is formed of a metal and has an opening for taking out the terahertz wave therethrough.

11. A device according to claim 8, wherein the spacer layer is composed of a high resistivity Si.

12. A device according to claim 8, wherein the spacer layer is composed of organic resin.

* * * * *